(12) United States Patent
Jenck et al.

(10) Patent No.: US 6,391,873 B1
(45) Date of Patent: May 21, 2002

(54) IMIDAZODIAZEPINE DERIVATIVE

(75) Inventors: François Jenck, Riedisheim (FR);
Fabienne Hoffmann-Emery, Birsfelden (CH); Walter Hunkeler, Magden (CH); James Richard Martin, Therwil (CH); Andrew Sleight, Riedisheim (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/566,832

(22) Filed: May 8, 2000

(30) Foreign Application Priority Data

May 12, 1999 (EP) .............................. 99109513

(51) Int. Cl.$^7$ ............................................. A61K 31/555
(52) U.S. Cl. ........................................ 514/220; 540/499
(58) Field of Search .......................... 514/220; 540/499

(56) References Cited

U.S. PATENT DOCUMENTS 5,665,718 A   9/1997   Godel et al.
6,174,881 B1 * 1/2001   Borer et al. ................ 514/220

FOREIGN PATENT DOCUMENTS

EP      672 666      9/1995

OTHER PUBLICATIONS

Derwent Abstract of European Patent No. 672 666 (Document B1).

Martin & Haefely, Drugs used for the Treatment of Anxiety and Sleep Disorders, Principles of Pharmacology: Bassic Concepts and Clinical Applications, edited by P. Munson et al., New York, pp. 243–277 (1995).

Mohler et al., Agonist and antagonist benzodiazepine receptor interaction in vitro, Nature, vol. 294, pp. 763–765 (1981).

Mohler et al., Benzodiazepine Antagonist Ro 15–1788: Binding Charactristics and Interaction with Drug–Induced Changes in Dopamine turnover and Cerebellar Cgmp Levels, J. Neurochemistry, vol. 37, pp. 714–732 (1981).

Y. Cheng and W. H. Prusoff, Relationship between the Inhibition Constant (Ki) and the Concentration of Inhibitor which causes 50 percent Inhibition (IC50) of an Enzymatic Reaction, Biochem, Pharmac., vol. 22, pp. 3099–3108 (1973).

Martin et al., Acute and Chronic Administration of Buspirone Fails to Yield Anxiolytic–like Effects in a Mouse Operant Punishment Paradigm, Pharmacol. Biochem. Behave., vol. 46, pp. 905–910 (1993).

* cited by examiner

Primary Examiner—James H. Reamer
(74) Attorney, Agent, or Firm—George W. Johnston; Patricia S. Rocha-Tramaloni; Arthur D. Dawson

(57) ABSTRACT

The present invention relates to compound 7-Chloro-3-(5-dimethylaminomethyl-[1,2,4]oxadiazol-3-yl)-5-methyl-4,5-dihydro-imidazo[1,5-a][1,4]benzodiazepin-6-one (I)

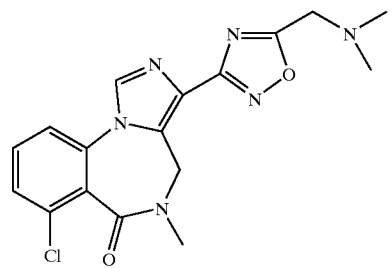

and to the use of the compound of formula I for the manufacture of medicaments to be used as anxiolytic and/or anticonvulsant and/or non-sedative sleep-inducing medicaments.

8 Claims, No Drawings

IMIDAZODIAZEPINE DERIVATIVE

CROSS REFERENCE TO RELATED APPLICATION

The present application is related to copending application Ser No. 09/566,831, filed on even date herewith, entitled "Method of Making Diazepine Derivatives," by inventor F. Emery, examples 1 and 11 of which are hereby incorporated by reference.

BACKGROUND

Conventional benzodiazepine anxiolytics are often associated with adverse effects such as motor impairment, excessive sedation, tolerance for the therapeutic effect, physical dependence, abuse liability, cognitive impairments, or toxic effects in overdose. The benzodiazepine of the present invention is useful for treating acute and chronic anxiety disorders (including but not limited to generalized anxiety disorder, panic disorder, social and other phobias, post-traumatic stress disorder, acute anxiety crises) and is not only rapid acting and efficacious in mild-to-severe anxiety disorders and effective when given daily (as once daily, b.i.d. or t.i.d) but shows either no, or substantially less, of the above mentioned adverse side effects.

SUMMARY OF THE INVENTION

The present invention relates to 7-Chloro-3-(5-dimethylaminomethyl-[1,2,4]oxadiazol-3-yl)-5-methyl-4,5-dihydro-imidazo[1,5-a][1,4]benzodiazepin-6-one (I)

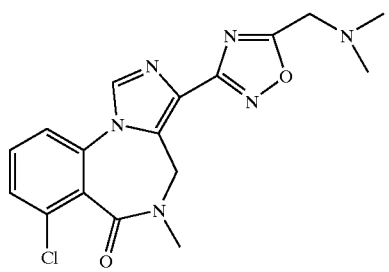

and pharmaceutically acceptable acid addition salts thereof.

This compound and its salts are novel and have valuable pharmacodynamic properties. They are therefore suitable for therapeutic purposes, especially for anxiolytic and/or anti-convulsant purposes and/or for the non-sedative treatment of insomnia across a dose range in which no appreciable sedation and/or motoric impairment occurs.

Objects of the present invention are the above mentioned compound and salts thereof per se and as therapeutically active substances, their manufacture and their use for therapeutic purposes or for the production of corresponding medicaments, as well as medicaments containing the above compound or a salt thereof and the production of such medicaments.

DETAILED DESCRIPTION OF THE INVENTION

The compound of the invention and its pharmaceutically acceptable acid addition salts can be manufactured, for instance, according to the synthesis path depicted in Reaction Scheme 1

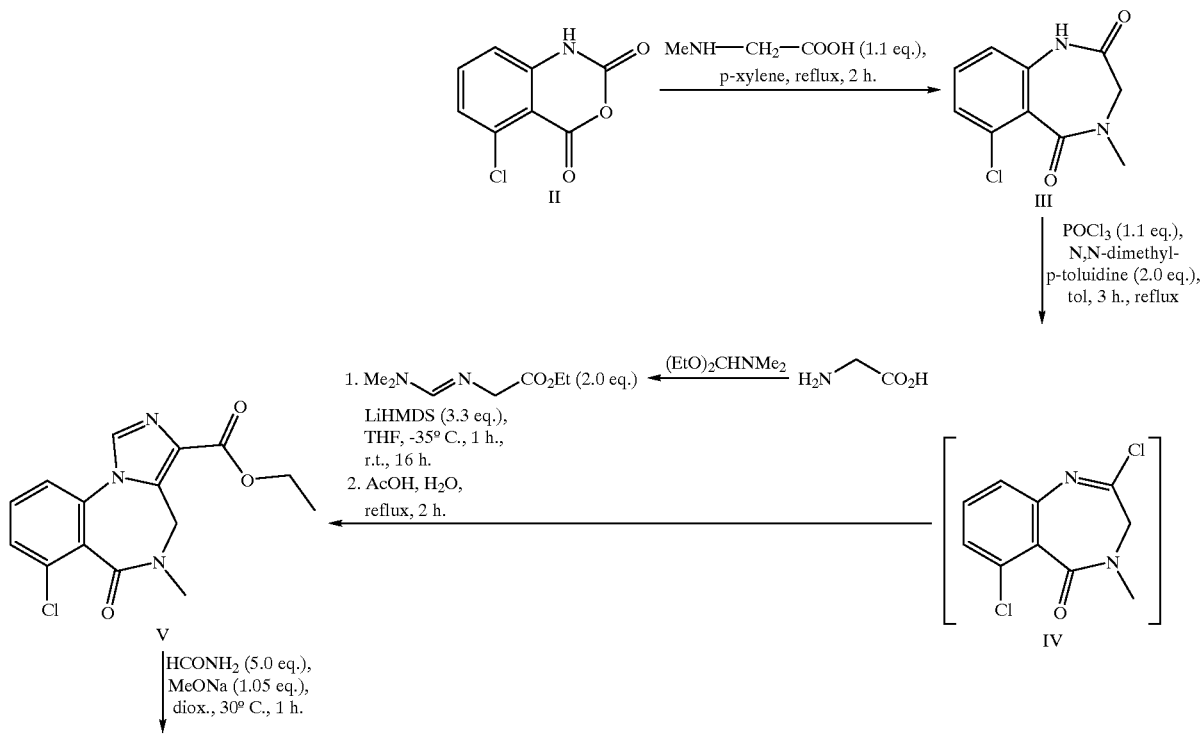

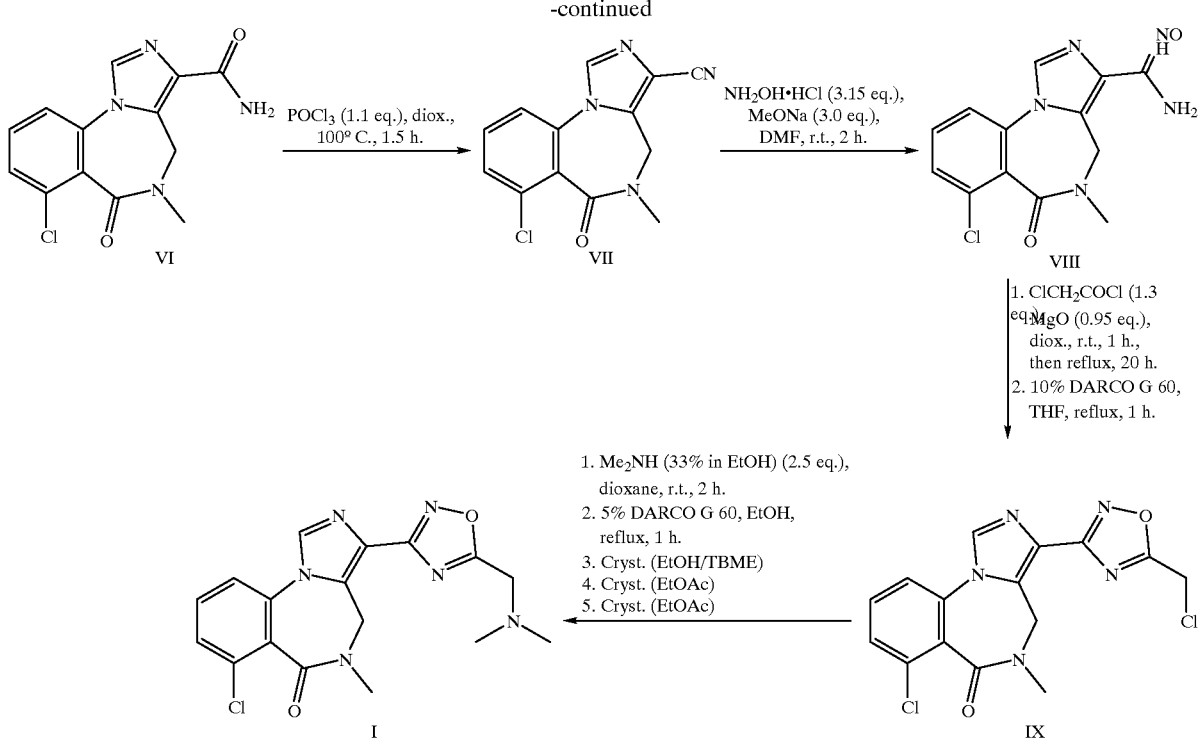

The benzodiazepine according to the present invention exhibits high affinity in vitro binding to benzodiazepine receptors, as well as rapid onset and robust therapeutic effects in such indications as anxiety disorders, insomnia, mood disorders, psychotic symptoms and disorders, and convulsive disorders (see: Hollister, L. E. et al., Clinical uses of benzodiazepines. *J. Clin. Psychopharmacol.* 13 (Suppl. 1): 1S–169S, 1993).

In particular, the benzodiazepine of the present invention is useful for treating acute and chronic anxiety disorders (including but not limited to generalized anxiety disorder, panic disorder, social and other phobias, post-traumatic stress disorder, acute anxiety crises) and is not only rapid acting and efficacious in mild-to-severe anxiety disorders and effective when given daily (as once daily, b.i.d. or t.i.d) but shows either no, or substantially less, adverse effects of the sorts characteristic of the known conventional benzodiazepine anxiolytics, such as motor impairment, excessive sedation, tolerance for the therapeutic effect, physical dependence (and the resultant withdrawal symptoms), abuse liability (i.e., psychological dependence), cognitive impairments, drug interactions due to different causes (especially interaction with ethanol or with substances commonly used within that patient population), or toxic effects in overdose (due either to exaggerated pharmacological effects or to non-specific effects of the compound itself at high doses). The pharmacological profile of the compound according to the present invention involves a clear separation between the therapeutic dose range and the doses producing adverse effects based on the results obtained in animals.

The preclinical pharmacological profile of the compound of the present invention for treatment of anxiety disorders, and/or treatment of convulsions and/or non-sedative treatment of sleep disorders involves no, or only minimal motor impairment, in a standard test of motor performance in animals (e.g. rotarod test in mice with motor function evaluated in the same animals at different time points up to 1 hour after intravenous injection). It has been shown for the compound of the present invention that the $ED_{50}$ (or doses producing impairment in 50% of the animals) for a rotarod deficit is greater than about 10 mg/kg i.v., and this is consistently observed at different time points across the entire period of measurement. Moreover, the pharmacological profile of the compound of the present invention involves a very high affinity in vitro binding to the benzodiazepine receptor ($^3$H-flumazenil in vitro binding assay using homogenized rat cortex) with a $pK_i$ value of 9.1 together with a potent anxiolytic-like effect in a mouse model of anxiety.

The compound of the present invention has shown, in the pre-clinical stage, further advantages which overcome several problems typical of the known conventional products. For example, not only is it active in a mouse model of anxiety but additionally it has shown low ethanol interaction in mice, minimal withdrawal signs in chronically treated mice subsequently challenged with a benzodiazepine receptor antagonist (e.g., sarmazenil), minimal reduction (so-called tolerance) of the anxiolytic effect in mice after chronic treatment, or minimal cognitive impairment in rats. In addition, low doses of the benzodiazepine of the present invention are active in an animal model of anxiety and show anticonvulsant effects in animals (for paradigm examples see: Martin & Haefely, Drugs used for the treatment of anxiety and sleep disorders. In: *Principles of Pharmacology: Basic Concepts and Clinical Applications*, edited by P. Munson et al., New York: Chapman & Hall, 1995, pp. 243–277). Moreover, the benzodiazepine according to the present invention produces minimal or no inhibition of cytochrome P450 isoenzymes, thus reducing the risk of drug-drug interactions due to metabolic cause.

The affinity of the compound of the invention to the central benzodiazepine receptors was established in vitro according to the methods described in *Nature* 294, 763–765 (1981) and *J. Neurochemistry* 37, 714–722 (1981). According to these methods, the inhibition of the binding of tritiated flumazenil to the specific benzodiazepine receptors in the cortex of rats by the respective test substance is determined. The affinity was calculated as $pK_i$ (for background information on $pK_i$ see: Cheng, Y. and W. H. Prusoff, Relationship between the inhibition constant ($K_i$) and the concentration of inhibitor which causes 50 percent inhibition ($IC_{50}$) of an enzymatic reaction. *Biochem. Pharmac.* 22: 3099–3108, 1973) as the measure of the specific binding of tritiated flumazenil to specific benzodiazepine receptors in the cortex of rat.

The motor impairing properties of the compound of the invention can be determined, for example, in the rotating rod test (rotarod test). Mice (Ibm: MORO (SPF); RCC Ltd., 4414 Füllinsdorf, Switzerland) weighing about 20–30 g are used for this test. These mice were housed in Macrolon® type I cages for one or more days following arrival in the laboratory colony (12:12 hour light-dark cycle). They have free access to a standard rodent diet (Kliba Mühlen, Kaiseraugst, Switzerland) and tap water in the home cage up to testing. They are brought into the test laboratory at least 30 min before the test which was done during the light portion of the day-night cycle. In the rotating rod test the animals are placed on a horizontally arranged, smooth metal rod having a diameter of 3 cm, which is rotated at 2 revolutions per min. Initially, the animals are given the opportunity of familiarizing themselves with the test situation for at least 30 sec. Subsequently, those animals which succeed in remaining on the rod for at least 1 min are selected for use in the test. These selected animals are then given the test preparations intravenously in different dosages. At various points in time post-injection, it is then determined whether the animals are able to remain wallking on the rod for a minimum period (minimum period of 10 sec at time points 15 sec. 30 sec. 1 min and 2 min; minimum period of 1 min at time points 5 min, 15 min, 30 min, 60 min). The dosage at which 50% of the animals are capable of remaining on the rod (i.e., $ED_{50}$) was determined at each of these time points.

The results which have been obtained with the compound of the invention in the tests described previously are compiled in the following Table.

| Affinity to benzo-diazepine receptors | Rotating rod test ($ED_{50}$ in mg/kg i.v.) determined at the following points in time after administration | | | | | | | |
|---|---|---|---|---|---|---|---|---|
| | 15 sec | 20 sec | 60 sec | 2 min | 5 min | 15 min | 30 min | 60 min |
| $pK_i$ = 9.1 | >10 | >10 | >10 | >10 | >10 | >10 | >10 | >10 |

The in vivo agonistic activity of the compound of the invention at benzodiazepine receptors was demonstrated in the mouse operant conflict model of anxiety (for experimental details see: Martin et al., Acute and chronic administration of buspirone fails to yield anxiolytic-like effects in a mouse operant punishment paradigm. *Pharmacol Biochem. Behav.* 46: 905–910, 1993). In brief, adult female albino mice [Ibm:MORO(SPF); RCC Ltd., 4414 Füllinsdorf, Switzerland] weighing approximately 30–40 g were used once they had been well trained over several months. The mice were individually housed in Macrolon® type I plastic cages with sawdust bedding. Tap water was available to the mice ad libitum, whereas access to the standard laboratory chow (Kliba Mühlen, Kaiseraugst, Switzerland) was restricted. Throughout the experiment the mice were maintained at approximately 80–85% of their free feeding body weight. Daily testing was done between 7 a.m. and 5 p.m. Such food-deprived mice were first trained to press a lever in a sound-attenuated operant box (circa 17×18×21 cm) in order to receive a 20-mg food pellet (Formula A/I; P. J. Noyes Company, Inc., Lancaster, N. H., USA) which was delivered into a food cup. Training sessions were 20 min and were generally given each weekday. Once a stable pattern of responding had been established, a new experimental phase was introduced: in 1 or 2 sessions per week (so-called "conflict tests"), an initial 5-min period during which each lever press was reinforced with a single food pellet was followed by an unsignaled 15-min period during which each lever press produced both a mild scrambled shock delivered through the stainless-steel grid floor and concomitant presentation of a single food pellet. In subsequent conflict tests, the mice received any of several reference benzodiazepine receptor full agonists (e.g., diazepam) or vehicle prior to testing. Only those mice who exhibited robust and stable drug-induced enhancement of punished responding were retained for use in subsequent experiments to investigate potential anxiolytics. Successive drug exposures were separated by a washout period of at least one week. Treatment was administered as an oral bolus circa 30 min prior to a conflict test. The evaluation lever-pressing within the punished portion of a conflict test session provides an accurate indication of the anxiolytic potential of a given compound. Data for each drug dose were compared separately with those of the vehicle condition (mean value for vehicle tests which were interspersed among the tests with drug) in the same animals using a one-tailed Wilcoxon matched-pairs, signed-rank test with a p-value equal or less than 0.05 accepted as statistically significant. The minimum effective dose (with statistically significant anxiolytic-like effect) for the compound of the invention was 3 mg/kg p.o. which indicates that it exhibits a potent anxiolytic-like effect typical of other benzodiazepine receptor agonists (e.g., diazepam).

Despite its exhibiting high affinity in vitro binding to benzodiazepine receptors, the compound of the invention nonetheless failed to reach an $ED_{50}$ for rotarod impairment up to 10 mg/kg i.v. Having regard to its agonistic activity on the benzodiazepine receptors (e.g. active in the mouse operant conflict model), the compound of the invention can be used, for example, as an anxiolytic (tranquilizer), and/or an anticonvulsant, and/or for the non-sedative treatment of insomnia with the important advantage that these therapeutically relevant effects can be obtained across a wide dose range in the absence of appreciable sedation and/or motoric impairment.

The compound of the present invention was administered to mice in the above described rotarod test up to 100 mg/kg i.v. without fatalities occurring. In addition, rats (Ibm: RORO (SPF); RCC Ltd., 4414 Füllinsdorf, Switzerland) received the compound of the present invention at 100 mg/kg i.v. without fatalities occurring.

The compound of the invention and pharmaceutically acceptable acid addition salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compound of the invention and pharmaceutically acceptable acid addition salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, saccharose, invert sugar, glucose and the like. Adjuvants such as alcohols, polyols, glycerol, vegetable oils and the like can be used for aqueous injection solutions of water-soluble acid addition salts of the compound of the invention, but as a rule are not necessary. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, coating agents or antioxidants. They can also contain other therapeutically valuable substances.

It is an object of the present invention to provide medicaments containing the compound of the invention or a pharmaceutically acceptable acid addition salt thereof and a therapeutically inert excipient.

A further object of the present invention is a process for the production of such medicaments which comprises bringing the compound of formula I or pharmaceutically acceptable acid addition salts thereof and, if desired, one or more other therapeutically valuable substances into a galenical administration form together with one or more therapeutically inert carriers.

The compound of the invention and pharmaceutically acceptable acid addition salts thereof can be used in accordance with the invention for therapeutic purposes, especially for anxiolytic and/or anticonvulsant and/or for the non-sedative treatment of insomnia. The dosage can vary within wide limits and will, of course, be fitted to the individual requirements in each particular case. In general, in the case of oral administration a daily dosage of about 1 mg to 1000 mg should be appropriate. For intravenous or rectal administration a daily dosage of about 1 mg to 100 mg should be appropriate.

Finally, it is also an object of the present invention to provide the use of the above compound and of pharmaceutically usable acid addition salts thereof for the manufacture of medicaments, to be especially used as non-sedative and non-motor-impairing anxiolytic and/or anticonvulsant and/or non-sedative sleep-inducing medicaments.

The following example is intended to illustrate the present invention in more detail, but is not intended to limit its scope in any manner. A method of making an intermediate useful in the following example is disdosed in copending application Ser. No. 09/566,831, filed on even date herewith, entitled "Method of Making Diazepine Derivatives," by inventor F. Emery, examples 1 and 11 of which are hereby incorporated by reference.

EXAMPLE a) 6-Chloro-3,4-dihydro-4-methyl-2H-1,4-benzodiazepine-2,5(1H)-dione (III)

25.0 g 6-chloro-isatoic anhydride (II) and 12.4 g sarcosine were suspended under stirring and argon atmosphere in 100 ml p-xylene and heated at reflux for two hours. The suspension was cooled to room temperature and further stirred 1 hour, then filtered off. The precipitate was washed with 25 ml p-xylene twice and dried at 50° C. under vacuum. The solid so obtained (6-chloro-3,4-dihydro-4-methyl-2H-1,4-benzodiazepine-2,5(1H)-dione (III)) was digested in 75 ml deionized water at 0° C. for 1 hour, filtered off, washed with 25 ml deionized water and dried under vacuum 18 hours at 80° C. Crude product: 25.2 g as a beige powder. m.p. 230–232° C.

b) Ethyl 7-chloro-5,6-dihydro-5-methyl-6-oxo-4H-imidazo[1,5-a][1,4]benzodiazepine-3-carboxylate
(V)

25.0 g 6-Chloro-3,4-dihydro-4-methyl-2H-1,4-benzodiazepine-2,5(1H)-dione (III) were suspended under stirring and argon atmosphere in 200 ml toluene and 32.1 ml N,N-dimethyl-p-toluidine. The suspension was heated to 100° C. and 11.2 ml phosphorus oxychloride were added over 30 minutes and stirring was pursued two and an half hours at 100° C. The dark-orange solution was cooled to 40° C. and toluene was removed under reduced pressure to give 82 g of a dark-orange oil.

Meanwhile, 81.2 ml hexamethyldisilazane and 265 ml tetrahydrofuran were mixed and cooled to −35° C. 229.5 ml Butyllithium were added over 45 minutes and, after stirring 30 minutes at −35° C., a solution of 35.2 g ethyl (dimethylamino-methylenamino)acetate in 70.4 mnl tetrahydrofuran was added over 30 minutes. The orange solution obtained was stirred one more hour at −35° C. and a solution of the crude iminochloride in 100 ml tetrahydrofuran was added over 1 hour at −15° C. The dark red solution was stirred one hour at −15° C., then 18 hours at room temperature (r.t.). 75 ml Acetic acid were added in 10 minutes, then 75 ml deionized water were added in one portion and the orange suspension was heated at reflux for two hours. Tetrahydrofuran was removed under reduced pressure and the residue was partitioned between 200 ml dichloromethane and 100 ml deionized water. The phases were separated and the organic phase was washed with 100 ml aqueous HCl 1N twice and with 100 ml deionized water. The aqueous phases were extracted twice with 100 ml dichloromethane. The combined organic extracts were dried ($Na_2SO_4$) and evaporated. The residue was digested in 200 ml n-heptane 30 minutes at r.t. and filtered off. The sticky crystals obtained were digested at reflux for 30 minutes in 213.5 ml ethanol, then stirred 3 hours to r.t. and 2 hours at −20° C. The precipitate (ethyl 7-chloro-5,6-dihydro-5-methyl-6-oxo-4H-imidazo[1,5-a][1,4]benzodiazepine-3-carboxylate (V)) was filtered off, washed three times with 20 ml ethanol and dried under reduced pressure 16 hours at 60° C. Crude product: 23.4 g as a beige powder. m.p. 225.5–226.5° C.

c) 7-Chloro-5,6-dihydro-5-methyl-6-oxo-4H-imidazo[1,5-a][1,4]benzodiazepine-3-carboxamide
(VI)

22.8 g Ethyl 7-chloro-5,6-dihydro-5-methyl-6-oxo-4H-imidazo[1,5-a][1,4]-benzodiazepine-3-carboxylate (V)were suspended under stirring and argon atmosphere in 91.2 ml 1,4-dioxane. 14.1 ml Formamide and 13.9 ml sodium methanolate were successively added to yield a clear light-orange solution, which turned to a white suspension after 10 minutes. This suspension was stirred two hours at 30° C. 200 ml deionized water were added in one portion and 1,4-dioxane was distilled off at 40° C. under reduced pressure. The remaining white suspension was stirred two hours at 0° C. and filtered. The precipitate (7-chloro-5,6-dihydro-5-methyl-6-oxo-4H-imidazo[1,5-a][1,4]benzodiazepine-3-carboxamide (VI)) was washed with 50 ml deionized water three times and dried under reduced pressure for 18 hours at 80° C. Crude product: 19.43 g as a white powder. m.p.>250° C.

d) 7-Chloro-5,6-dihydro-5-methyl-6-oxo-4H-imidazo[1,5-a][1,4]benzodiazepine-3-carbonitrile (VII)

19.0 g 7-Chloro-5,6-dihydro-5-methyl-6-oxo-4H-imidazo[1,5-a][1,4]benzodiazepene-3-carboxamide (VI) were suspended under stirring and argon atmosphere in 95 ml 1,4-dioxane and 6.58 phosphorous oxychloride were added in one portion. The reaction mixture was heated to reflux for one hour giving a yellow solution, which was concentrated at 50° C. under reduced pressure. The residue was digested in 100 ml deionized water for two hours at r.t. The precipitate (7-chloro-5,6-dihydro-5-methyl-6-oxo-4H-imidazo[1,5-a][1,4]benzodiazepine-3-carbonitrile (VII)) was filtered off, washed three times with 30 ml deionized water and dried under vacuum at 80° C. for 18 hours. Crude product: 17.3 g as a light yellow powder. m.p. 238.5–239.5° C.

e) 7-Chloro-5,6-dihydro-5-methyl-6-oxo-4H-imidazo[1,5-a][1,4]benzodiazepine-3-carboxamidoxime (VIII)

16.8 g 7-Chloro-5,6-dihydro-5-methyl-6-oxo-4H-imidazo[1,5-a][1,4]benzodiazepine-3-carbonitrile (VIII) were suspended under stirring and argon atmosphere in 101 ml N,N-dimethylformamide and 13.48 g hydroxylamine hydrochloride was added in one portion. 34.2 ml Sodium methanolate were then added over 60 minutes to the yellow suspension, which turned to a colorless suspension. It was stirred one more hour at r.t., then cooled to 0–2° C. and 202 ml deionized water were added over 30 minutes. After stirring one more hour at 0° C., the precipitate (7-chloro-5,6-dihydro-5-methyl-6-oxo-4H-imidazo[1,5-a][1,4]benzodiazepine-3-carboxamidoxime (VIII) was filtered off, washed twice with 40 ml deionized water and dried under vacuum at 70° C. for 18 hours. Crude product: 17.84 g as a white powder. m.p.>250° C.

f) 7-Chloro-3-(5-chloromethyl-[1,2,4]oxadiazol-3-yl)-5-methyl-4,5-dihydro-imidazo[1,5-a][1,4]benzodiazepin-6-one (IX)

8.0 g 7-chloro-5,6-dihydro-5-methyl-6-oxo-4H-imidazo[1,5-a][1,4]benzodiazepine-3-carboxamidoxime (VIII) and 1.0 g magnesium oxide were suspended under stirring and argon atmosphere in 160 ml 1,4-dioxane. 2.7 ml Chloracetyl chloride were added in one portion and the white thick gel obtained was stirred 4 hours at r.t. and then 17 hours at reflux to give a lightly orange fluid suspension. 100 ml Dioxane were distilled off and the reaction mixture was cooled to room temperature. 180 ml Deionized water were added within 15 minutes and the suspension was stirred 1 hour at r.t. The precipitate was filtered off, washed with 50 ml deionized water twice and dried under vacuum at 80° C. for 18 hours. Crude product: 8.3 g as a light pink powder. This crude product was dissolved in 120 ml tetrahydrofuran at reflux and 0.83 g active charcoal Darco G 60 were added. The system was refluxed 1 hour, then filtered on 25 g Dicalit-Speedex and the filter cake was washed with three portions of 50 ml warm tetrahydrofuran. The filtrate was concentrated at 40° C. under reduced pressure. The residue was digested in 80 ml ethanol 1 hour at reflux, then stirred 16 hours at r.t. and finally 2 hours at 2° C. The precipitate (7-chloro-3-(5-chloromethyl-[1,2,4]oxadiazol-3-yl)-5-methyl-4,5-dihydro-imidazo[1,5-a][1,4]benzo-diazepin-6-one (IX)) was filtered off, washed with 2 portions of 25 ml cold tert-butyl methyl-ether and dried under vacuum 5 hours at 80° C. Crude product: 7.6 g as a light beige powder. m.p. 234–238° C.

g) 7-Chloro-3-(5-dimethylaminomethyl-[1,2,4]oxadiazol-3-yl)-5-methyl-4,5-dihydro-imidazo[1,5-a][1,4]benzodiazepin-6-one (I)

7.0 g 7-Chloro-3-(5-chloromethyl-[1,2,4]oxadiazol-3-yl)-5-methyl-4,5-dihydro-imidazo-[1,5-a][1,4]benzodiazepin-6-one (IX) were suspended under stirring and argon atmosphere in 70 ml 1,4-dioxane and 25.7 ml dimethylamine (33% in ethanol) were added over 60 minutes. The reaction mixture was stirred one more hour at r.t. and then the solvents were removed under reduced pressure at 35° C. The residue was partitioned between 50 ml dichloromethane and 20 ml deionized water. The phases were separated and the organic phase was washed twice with 20 ml deionized water. The aqueous phases were extracted separately with the same portion of 25 ml dichloromethane, twice. The combined organic extracts were dried (Na2SO4) and the solvent was removed under reduced pressure. Crude product: 8.0 g as a light yellow foam.

Purification

The crude product was dissolved in 40 ml ethanol at reflux and 400 mg active charcoal Darco G 60 were added. The system was stirred 1 hour at reflux, then filtered on a hot pad of Dicalit Speedex, which was washed with two portions of 40 ml hot ethanol. The filtrate was concentrated to 14 g under reduced pressure, heated to reflux and at this temperature and 40 ml tert-butyl-methylether were added over 5 minutes. The suspension was cooled slowly to r.t., stirred 16 hours, further cooled to 2° C. After stirring 1 hour at 2° C., the precipitate was filtered off, washed with 20 ml tert-butyl-methylether and dried 1 hour at 60° C. under vacuum. The so obtained powder was dissolved at reflux in 26 ml ethyl acetate. 6.5 ml Ethyl acetate were then distilled off and the turbid solution obtained was slowly cooled to r.t., then to 0° C. After 1 hour stirring at 0° C., the precipitate was filtered off, washed with 10 ml cold tert-butyl-methylether and dried under vacuum at 60° C. for 16 hours. The so obtained powder (7-chloro-3-(5-dimethylaminomethyl-[1,2,4]oxadiazol-3-yl)-5-methyl-4,5-dihydro-imidazo[1,5-a][1,4]benzodiazepin-6-one (I)) was crystallized a second time in 24.3 ml ethyl acetate according to the procedure described above. Product: 5.5 g as a white powder. m.p. 151.5–153° C.

7-Chloro-3-(5-dimethylaminomethyl-[1,2,4]oxadiazol-3-yl)-5-methyl-4,5-dihydro-imidazo[1,5-a][1,4]benzodiazepin-6-one maleate (1:1)

373 mg 7-Chloro-3-(5-dimethylaminomethyl-[1,2,4]oxadiazol-3-yl)-5-methyl-4,5-dihydro-imidazo[1,5-a][1,4]benzodiazepin-6-one (I) and 116 mg maleic acid were dissloved in 3 ml hot ethanol. The salt crystalized on cooling. The suspension was stirred for 10 min at 0° C. Filtration and drying afforded 460 mg 7-Chloro-3-(5-dimethylaminomethyl-[1,2,4]oxadiazol-3-yl)-5-methyl-4,5-dihydro-imidazo[1,5-a][1,4]benzodiazepin-6-one maleate (1:1) as a whit solid. m.p. 182–184° C.

Example A

7-Chloro-3-(5-dimethylaminomethyl-[1,2,4]oxadiazol-3-yl)-5-methyl-4,5-dihydro-imidazo[1,5-a][1,4]

benzodiazepin-6-one was used as the active substance for the production of tablets of the following composition:

| | |
|---|---|
| Active substance: | 25.0 mg |
| Lactose Monohydrate: | 177.5 mg |
| Starch Maize White: | 60.0 mg |
| Sodium Carboxymethylcellulose: | 12.0 mg |
| Povidone 30: | 15.0 mg |
| Talc: | 9.0 mg |
| Magnesium Stearate: | 1.5 mg |

What is claimed is:

1. A compound of formula I, 7-Chloro-3-(5-dimethylaminomethyl-[1,2,4]oxadiazol-3-yl)-5-methyl-4,5-dihydro-imidazo[1,5-a][1,4]benzodiazepin-6-one

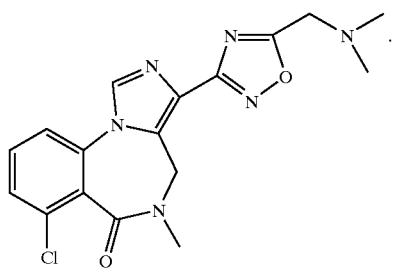

I

2. A pharmaceutical composition comprising a therapeutically effective amount of a compound of formula I

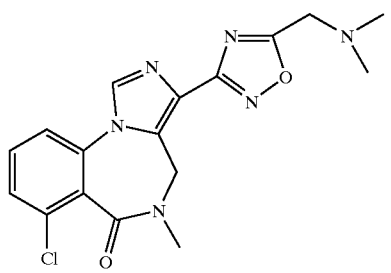

I as well as pharmaceutically salts of said compound and a pharmaceutically acceptable carrier.

3. A process for the manufacture of 7-chloro-3-(5-dimethylaminomethyl-[1,2,4]oxadiazol-3-yl)-5-methyl-4,5-dihydro-imidazo[1,5-a][1,4]benzodiazepin-6-one, comprising the amination of 7-chloro-3-(5-chloromethyl-[1,2,4] oxadiazol-3-yl)-5-methyl-4,5-dihydro-imidazo[1,5-a][1,4] benzodiazepin-6-one in the presence of dimethylamine.

4. A method of treating anxiety disorders in a mammal comprising administering to said mammal a compound of formula I

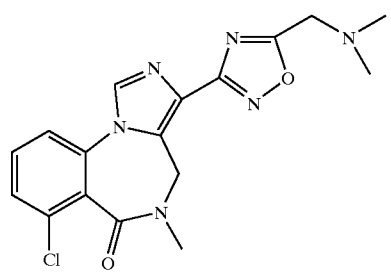

I as well as pharmaceutically acceptable salts of said compound and a therapeutically acceptable carrier in an amount which is effective in treating said anxiety disorder.

5. A method of treating insomnia in a mammal comprising administering to said mammal a compound of formula I

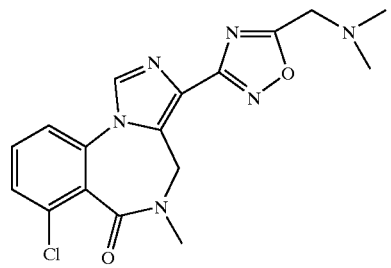

I as well as pharmaceutically acceptable salts of said compound and a therapeutically acceptable carrier in an amount which is effective in treating said insomnia.

6. A method of treating mood disorders in a mammal comprising administering to said mammal a compound of formula I

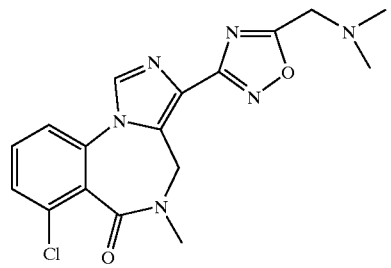

I as well as pharmaceutically acceptable salts of said compound and a therapeutically acceptable carrier in an amount which is effective in treating said mood disorder.

7. A method of treating psychotic symptoms in a mammal comprising administering to said mammal a compound of formula I

13

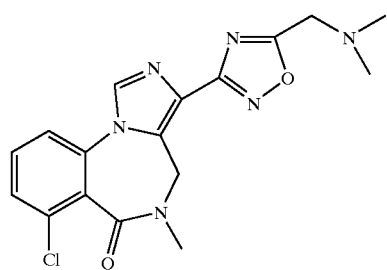

I as well as pharmaceutically acceptable salts of said compound and a therapeutically acceptable carrier in an amount which is effective in treating said psychotic symptoms.

8. A method of treating convulsive disorders in a mammal comprising administering to said mammal a compound of formula I

14

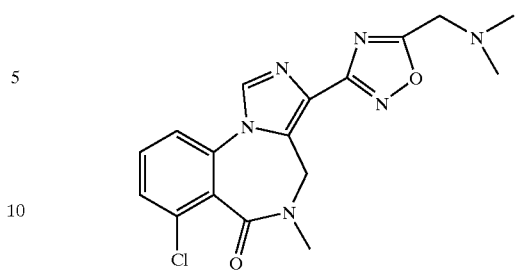

I as well as pharmaceutically acceptable salts of said compound and a therapeutically acceptable carrier in an amount which is effective in treating said convulsive disorders.

* * * * *